(12) United States Patent
Tang et al.

(10) Patent No.: US 8,314,261 B2
(45) Date of Patent: Nov. 20, 2012

(54) PROCESS FOR THE PREPARATION OF SYNTHETIC TAXANES

(75) Inventors: Dingning Tang, Guilin (CN); Jian Li, Guilin (CN)

(73) Assignee: Guilin Huiang Biochemistry Pharmaceutical Co. Ltd., Guilin (CN)

( * ) Notice: Subject to any disclaimer, the term of this patent is extended or adjusted under 35 U.S.C. 154(b) by 1101 days.

(21) Appl. No.: 10/585,794

(22) PCT Filed: Jan. 17, 2005

(86) PCT No.: PCT/CN2005/000068
§ 371 (c)(1),
(2), (4) Date: Aug. 12, 2008

(87) PCT Pub. No.: WO2005/073209
PCT Pub. Date: Aug. 11, 2005

(65) Prior Publication Data
US 2008/0287696 A1   Nov. 20, 2008

(30) Foreign Application Priority Data
Jan. 16, 2004 (CN) .......................... 2004 1 0021751

(51) Int. Cl.
*C07D 407/00* (2006.01)
(52) U.S. Cl. ...................................... 549/510; 549/511
(58) Field of Classification Search .................. 549/510, 549/511
See application file for complete search history.

(56) References Cited

U.S. PATENT DOCUMENTS

| | | | |
|---|---|---|---|
| 5,874,595 A | 2/1999 | Damen et al. | |
| 6,500,966 B1 * | 12/2002 | Bombardelli | 549/510 |
| 6,706,896 B1 * | 3/2004 | Holton et al. | 549/214 |
| 7,288,665 B1 * | 10/2007 | Holton et al. | 549/510 |
| RE40,120 E * | 2/2008 | Bombardelli | 549/510 |
| 7,589,111 B2 * | 9/2009 | Holton et al. | 514/337 |
| 7,667,055 B2 * | 2/2010 | Vu et al. | 549/510 |

FOREIGN PATENT DOCUMENTS

| | | |
|---|---|---|
| CN | 1241565 | 1/2000 |
| CN | 1239476 | 2/2006 |
| EP | 1285920 | 2/2003 |
| EP | 1170293 | 5/2006 |
| WO | 99/09021 | 2/1999 |
| WO | 00/49006 | 8/2000 |
| WO | 02/46177 | 6/2002 |
| WO | 2004/007473 | 1/2004 |

OTHER PUBLICATIONS

Breslow, R. et al., "*Geometrically Directed Selective Steroid Hydroxylation with High Turnover by a Fluorinated Artificial Cytochrome P-450*", Tetrahedron Letters 39 (1998) 2887-2890.
EP patent application No. 05700442.6, Examination Report mailed Jul. 4, 2011.
EP patent application No. 05700442.6, Office Action mailed Mar. 26, 2012.
Holton, Robert A. et al., "Selective Protection of the C(7) and C(10) Hydroxyl Groups in 10-Deacetyl Baccatin III," Tetrahedron Letters 39 (1998) 2883-2886, Feb. 13, 1998.

* cited by examiner

*Primary Examiner* — Andrew D Kosar
*Assistant Examiner* — Raymond Covington
(74) *Attorney, Agent, or Firm* — Weaver Austin Villeneuve & Sampson LLP

(57) ABSTRACT

The present invention relates to a process for the preparation of synthetic taxanes, which protects C(7)-OH with lanthanon compounds. Its advantages are simple process and firm & reliable binding. Moreover, no C(7)-acylated taxanes are produced in the subsequent steps, and hydrolysis of C(2')-ester groups in acylated products becomes readily controllable. In the process for the preparation of synthetic taxanes, tetrahydrofuran is used in the present invention as a medium for acylation, which not only achieves the same effects as pyridine, but also avoids odor, so as to solve the problem regarding the extremely high requirements for the place of production. The present invention can be used for the preparation of not only semi-synthetic taxane using natural taxanes as raw material, but also full-synthetic taxane.

25 Claims, 11 Drawing Sheets

PROCESS FOR THE PREPARATION OF SYNTHETIC TAXANES

FIELD OF THE INVENTION

The present invention relates to a process for the preparation of synthetic taxanes.

BACKGROUND OF THE INVENTION

Cephalomannine, baccatin III, 10-deacetylbaccatin III, 10-deacetylpaclitaxel, 10-deacetylcephalomannine, 7-(1β-xyloxyl)-paclitaxel, 7-(1β-xyloxyl)-cephalomannine, 7-(1β-xyloxyl)-10-deacetylpaclitaxel and 7-(1β-xyloxyl)-10-deacetylcephalomannine and so on, in addition to the anticancer drug paclitaxel, can also be isolated from barks, leaves and roots of *Taxus baccata* plants by extraction. Some of said taxanes have certain anticancer activity, whereas some of them have no anticancer activity. However, they can be used for the preparation of paclitaxel or other taxanes (e.g., docetaxel) having high anticancer activities by the semi-synthetic method. There are not only many studies thereof, but also mature methods. In principle, there are three directions. One is to convert 7-(1β-xyloxyl)-taxanes; the second is to semi-synthesize paclitaxel by reacting side chains with paclitaxel parent nucleuses; and the third is to develop new non-natural taxanes by reacting different side chains with paclitaxel parent nucleuses. Semilh, et al have cracked 7-(1β-xyloxyl)-using the enzyme method (see J. Nat. Prod., 1984, 47, 131). Zhang Hongjie has hydrolyzed 7-(1β-xyloxyl)-paclitaxel with aqueous HCl in the presence of the catalyst LX-97615 (see the application of CN1241565A). In addition, the method of oxidative cracking 7-(1β-xyloxyl)-using periodates was widely used (see the applications of U.S. Pat. No. 5,200,534A, U.S. Pat. No. 5,367,086A and U.S. Pat. No. 5,856,532A). Furthermore, there are a plurality of patents and theses regarding the reaction of side chains with paclitaxel parent nucleuses. However, said studies inevitably need to solve the contradiction between the acylation of C(10)-OH and the protection of 2',7-OH. Currently, the general mode is to protect 2',7-OH with a protecting agent selected from the group consisting of multimethyl silane, multiethyl silane, multimethyl-(ethyl)chlorsilane, and chloracetate (chloracetic anhydride), then to acylate C(10)-OH using an acylating agent such as acetic anhydride or chloracetyl, and finally to deprotecting the protecting groups of 2',7-OH using a deprotecting agent such as thiourea. The typical method to solve the contradiction between the acylation and the protection is to use choroacetic acid (chloracetate) as a protecting agent, acetic anhydride as an acylating agent, thiourea as a deprotecting agent as disclosed in the application U.S. Pat. No. 5,200,534A. Nevertheless, the protective effects of said method are not quite satisfying, and about 11% 2',7,10-triacetyl taxane will be produced, which reduces the yield of the products obtained by acylating C(10)-OH and finally reduces the yield of 10-acetyltaxane. Although the products of 2',7-OH can be obtained by the hydrolysis of ester groups at C(2')- and C(7)-positions using a weak alkali, it is very difficult to completely hydrolyze esters at C(7)-position without affecting C(10)-position esters. Further, during the acylation, the inert solvents used in the previous processes are hydrochloric ethers, ethers, molecular silicons, aliphatic ketones and tertiary amine compounds etc. What's used most is pyridine which has the best effects. However, the odor of pyridine really smells unpleasant. When pyridine is in an amount less than $1 \times 10^{-6}$, there will have a strongly pungent odor. The maximum concentration acceptable in the air is $5 \times 10^{-6}$, and there are strict requirements for the obturation of the preparation apparatus and the air circulation in the place of production.

There are many published research findings for full-synthetic taxanes, but they are not formally used in the industrial production yet. The procedures for the preparation of full-synthetic taxanes involve synthetizing paclitaxel parent nucleuses from some chemical intermediates by the reaction comprising many steps, and men introducing relevant side chains at C-13-position. Due to the activities of C(7)-OH and C(10)-OH or C(10)-OAc, it cannot do without the protection of C(7)-OH and the acylation of C(10)-OH during said reaction. The previous methods of protection and acylation are the same as those of semi-synthetic taxanes, and thus mere are the same problems in the preparation process of semi-synthetic taxanes. Accordingly, as for full-synthetic taxanes, it is also a problem to be further studied to solve the contradiction between the protection and the acylation.

SUMMARY OF THE INVENTION

The object of the present invention is to provide an improved process for synthesizing taxanes.

The object of the present invention is achieved by the following disclosure.

One aspect of the present invention is to provide a process for the preparation of synthetic taxanes by improving the protection of C(7)-OH during the synthesis of taxanes, wherein said process makes the protection of C(7)-OH simple and reliable, and the deprotection is carried out without any specific deprotecting agent.

In the process for the synthesis of taxanes in the present invention, lanthanon compounds are used for the protection of C(7)-OH.

Said lanthanon compounds used in said process include a salt of lanthanon, a double salt of lanthanon, an alkaline compound of lanthanon, a lanthanon chloride, a lanthanon oxychloride, preferably a lanthanon chloride, a lanthanon hydroxide, a lanthanon oxychloride, a lanthanon sulfate double salt, more preferably a lanthanon chloride and a cerium salt, particularly preferably cerium trichloride.

The second aspect of the present invention is to provide a process for the preparation of synthetic taxanes by improving the acylation during the synthesis of taxanes. In order to improve the acylation in the process for the preparation of synthetic taxanes, tetrahydrofuran is used in the present invention as an acylation medium.

In said process, when tetrahydrofuran is used as an acylation medium, tetrahydrofuran is pre-dehydrated preferably.

The third aspect of the present invention is to provide a process for the preparation of synthetic taxanes, comprising (1) protecting C(7)-OH with a protecting agent; (2) acylating OH in taxanes with an acylating agent; and (3) deprotecting the protecting agent at C(7)-position to reduce to C(7)-OH, wherein tetrahydrofuran is used in said process as a medium for the acylation.

In the process for the preparation of synthetic taxanes as stated in any one of said aspects, the preferable synthetic taxanes are paclitaxels. In the present invention, it is found that lanthanon compounds have high selectivity for C(7)-OH in the paclitaxel parent nucleuses, and hardly react with C(2')-OH and C(10)-OH. Thus, lanthanon compounds as the protecting agent protect only C(7)-OH, and its advantages are simple process and firm & reliable binding. During the subsequent acylation, esterification takes place only at C(2')- and C(10)-positions, rather than at C(7)-position. As a result, the by-product, 2',7,10-triester taxane, will not be produced. Thereby, the yield of the principal product is increased, and the hydrolysis of C(2')-ester taxane becomes easier. The studies of C(2')-OH, C(7)-OH and C(10)-OH show that the activities of said three —OH are in an order of C(2')<C(7)<C(10), and that the hydrolysis difficulty after esterification by acylation is in an order of C(2')<C(7)<C(10). Provided that a triacetyl compound is formed, esters at C(10)-position are also easily hydrolyzed if esters at C(7)-position are completely hydrolyzed. Currently, there are no esters at C(7)-position in the present invention. By using the great difference in the difficulty between esters at C(2')-position and esters at C(10)-position, it is convenient to hydrolyze esters at C(2')-position as completely as possible by controlling the amount of alkali, and meanwhile hydrolyze esters at C(10)-position as less as possible, so as to increase the yield of the principal product, C(10)-acetyl taxane.

The inventor also finds that, after lanthanon compounds are used for protecting C(7)-OH in paclitaxel parent nucleuses, the subsequent deprotection becomes very easy, and no specific deprotecting agent is needed. Substances, such as alkali for neutralization, in many subsequent processing procedures, can be used for deprotection.

The inventor also finds that, after lanthanon compounds are used for protecting C(7)-OH in paclitaxel parent nucleuses, the subsequent acylation can be easily carried out. That is to say, lanthanon compounds catalytically promote the subsequent acylation.

In the process for the preparation of synthetic taxanes involving acylation, the reactants should be in solution, and the solvents should be inert in order to conduct acylation in a sufficient and complete way. In fact, the inert solvent functions only as a dissolvant or medium. Although there are many known inert solvents, which can be used as media for acylation, pyridine has the best effects. As stated above, it will bring about substantial difficulty in the production to use pyridine. In the present invention, tetrahydrofuran is used as a medium for acylation, which not only achieves the same effects as pyridine, but also avoids odor, so as to solve the problem regarding the extremely high requirements for the place of production. Tetrahydrofuran smells similar to ether, and the maximum concentration thereof acceptable in the work place is 100 mg/m$^5$.

The process for the preparation of synthetic taxanes in the present invention can be used for the preparation of not only semi-synthetic taxanes using natural taxanes as precursors, but also full-synthetic taxanes. This is because C(7)-OH should be necessarily protected, and other OH should be necessarily acylated during the preparation of full-synthetic taxanes.

In the process for the preparation of semi-synthetic taxanes, if 10-deacetyltaxanes are used as raw materials, the typical procedures are, for example, (1) protecting C(7)-OH with a protecting agent; (2) acylating C(10)-OH with an acylating agent, and meanwhile acylating C(2')-OH; and (3) hydrolyzing C(2')-ester groups with a weak alkali and meanwhile deprotecting the protecting agent at C(7)-position to reduce to C(7)-OH. After said three steps, 10-deacetyltaxanes are converted into 10-acetylpaclitaxels. Without any measures for increasing temperature, said three steps are carried out at normal temperature. However, in order to control the reaction rate, it is better to take some certain cooling measures during the third step of hydrolysis, such as ice bath, so as to carry out the reaction at a temperature $\leqq 3°$ C. When said lanthanon compounds are used for the protection of C(7)-OH, in order to simplify the process and to well connect the protection with the acylation, tetrahydrofuran is used as a medium for the protection of reaction. That is to say, tetrahydrofuran is firstly used to solve 10-deacetyltaxane, and then a protecting agent is added therein to carry out the reaction; after the compound in which C(7)-OH is protected is formed, an acylating agent such as acetic anhydride is directly added into the reactor to carry out the acylation, and finally producing 2',10-diacetyl ester taxane. In addition to acetic anhydride, there are chloracetyl and so on as common acylating agents. Other organic acid anhydride, such as succinic anhydride, propionic anhydride, benzoyl chloride, carbocyclephenyl-alanyl, butyryl chloride, nitrobenzoyl and cinnyl, can also be used for acylation, and the products obtained are taxanes of other 2',10-di-organic acid esters. No matter which acylating agent is used, the conditions of acylation are the same.

After the completion of acylation, the solvent immiscible with tetrahydrofuran can be used for the extraction of 2',10-diacyl ester taxane. In the present invention, there are no particular limitations to said solvent for extraction, and the preferable solvent is selected from the group consisting of dichloromethane and trichloromethane. After condensation, the liquid extract is dissolved in an inert organic solvent, and then cooled to a temperature $\leqq 3°$ C. Then, a weakly alkaline inert solution is added therein to selectively hydrolyze esters at C(2')-position, and simultaneously deprotect the protecting agent at C(7)-position, so as to reduce C(2')- and C(7)-positions to hydroxyl groups. In this connection, the inert solvent is preferably alcohols, more preferably methanol. Moreover, there are inorganic and organic weak alkalis, preferably sodium bicarbonate, potassium bicarbonate, dimethylamine, diethylamine, and aniline etc.

In addition, 7-(1β-xyloxyl)-10-deacetyltaxanes can also be used as raw materials for the preparation of semi-synthetic taxanes. Various effective methods, such as enzymolysis, hydrolysis, oxidative cracking and so on, are used to convert 7-(1β-xyloxyl)-into C(7)-OH, or convert into dialdehyde first, then to further oxidize it to C(7)-OH. It thus can be seen that such procedures are the same as those disclosed in the previous documents. After said procedures, 10-deacetyltaxanes are formed. Subsequently, the same process for the preparation of semi-synthetic taxanes using 10-deacetyltaxanes as raw materials can be used for the preparation of semi-synthetic taxanes.

There are many published research findings for full-synthetic taxanes, but they are not formally used in the industrial production yet. The procedures for the preparation of full-synthetic taxanes involve synthetizing paclitaxel parent nucleuses from some chemical intermediates by the reaction comprising many steps, and then introducing relevant side chains at C-13-position. Due to the activities of C(7)-OH and C(10)-OH or C(10)-OAc, the protection of C(7)-OH and the acylation of C(10)-OH are always necessary during said reaction. Currently, like the application in the preparation of semi-synthetic taxanes, the preparation process provided in the present invention can be completely applied in the preparation of full-synthetic taxanes.

After completion of said steps, various taxanes required can be obtained by the conventional skills, such as isolation, purification and crystallization no matter whether they are full-synthetic or semi-synthetic texanes.

BRIEF DESCRIPTION OF THE DRAWINGS

FIG. 7-1 shows an infrared spectrogram of natural cephalomannine.

FIG. 7-2 shows an infrared spectrogram of cephalomannine obtained by me present invention in Example 7.

EXAMPLES

Figure 1:
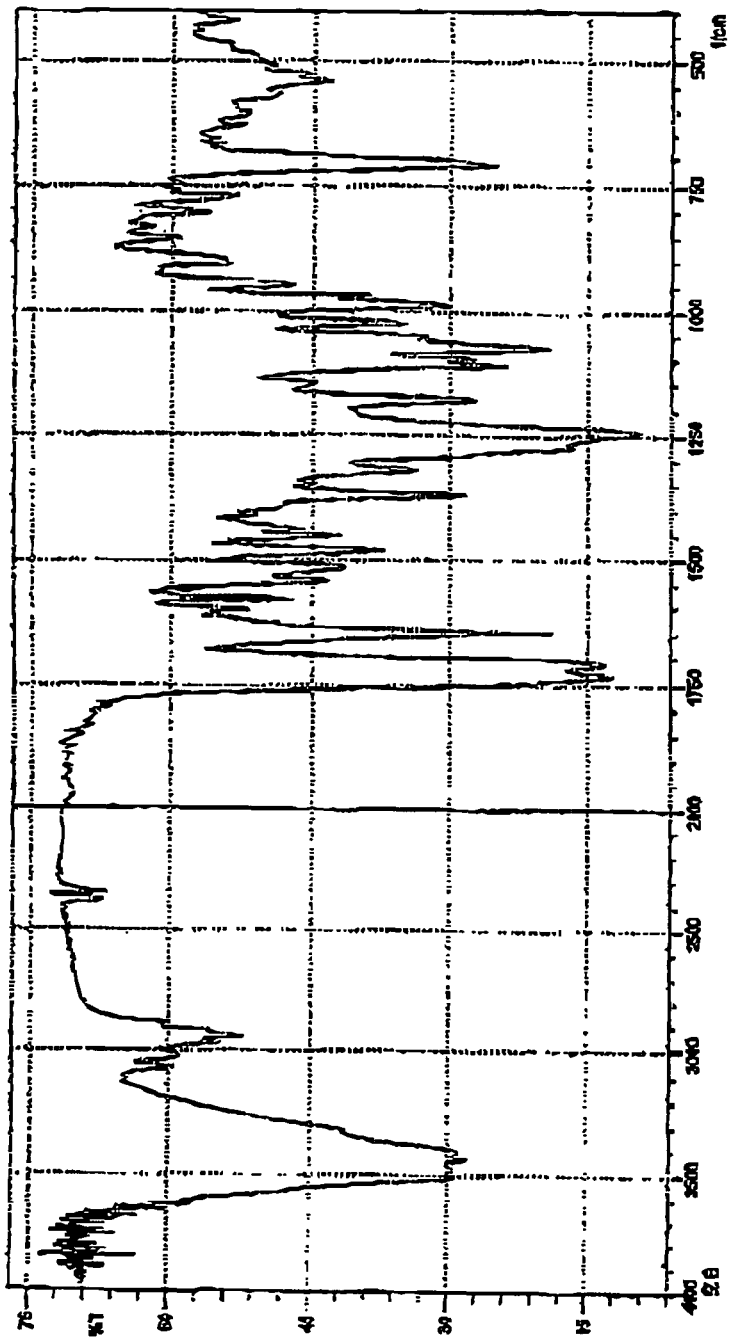
FIG. 1 shows an infrared spectrogram of the product obtained in Example 1.
Figure 2:
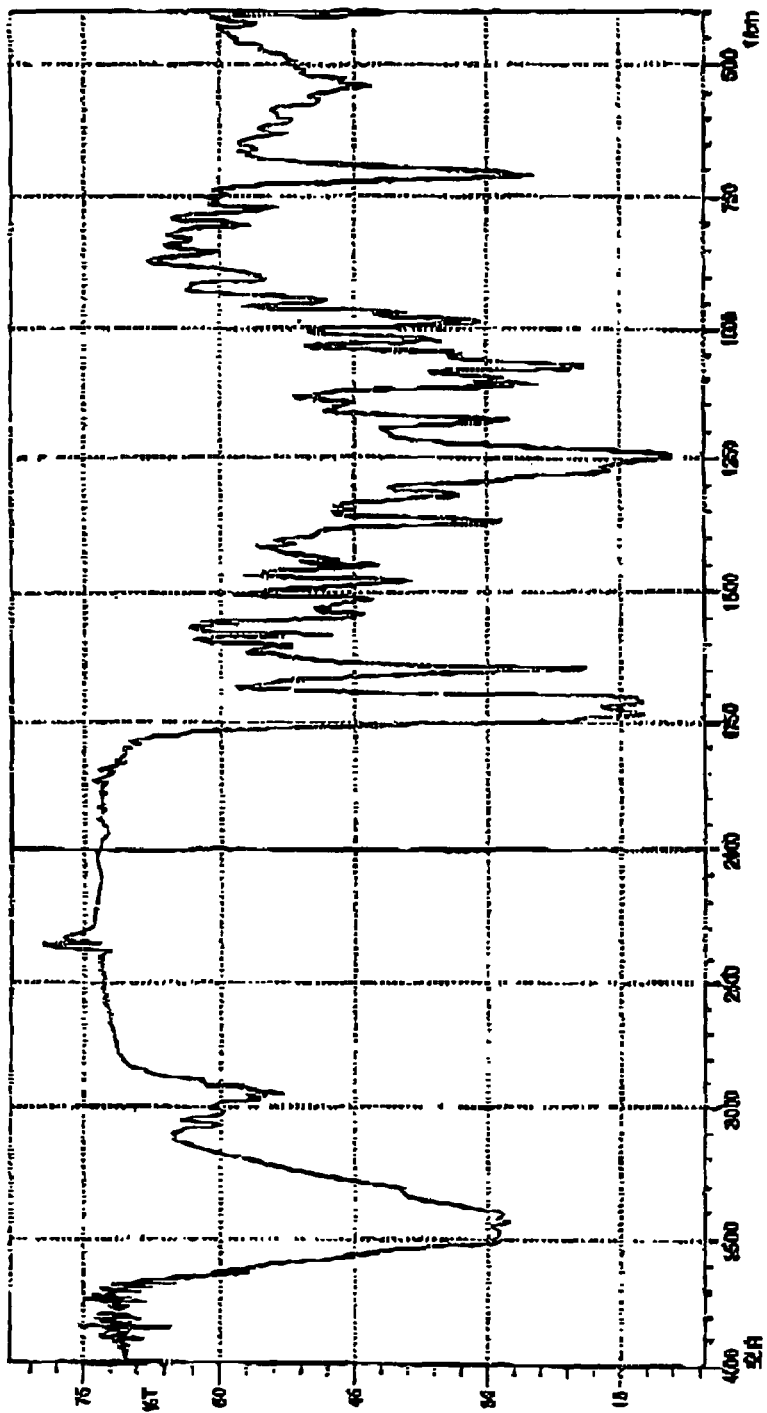
FIG. 2 shows an infrared spectrogram of the product obtained in Example 2.
Figure 3:
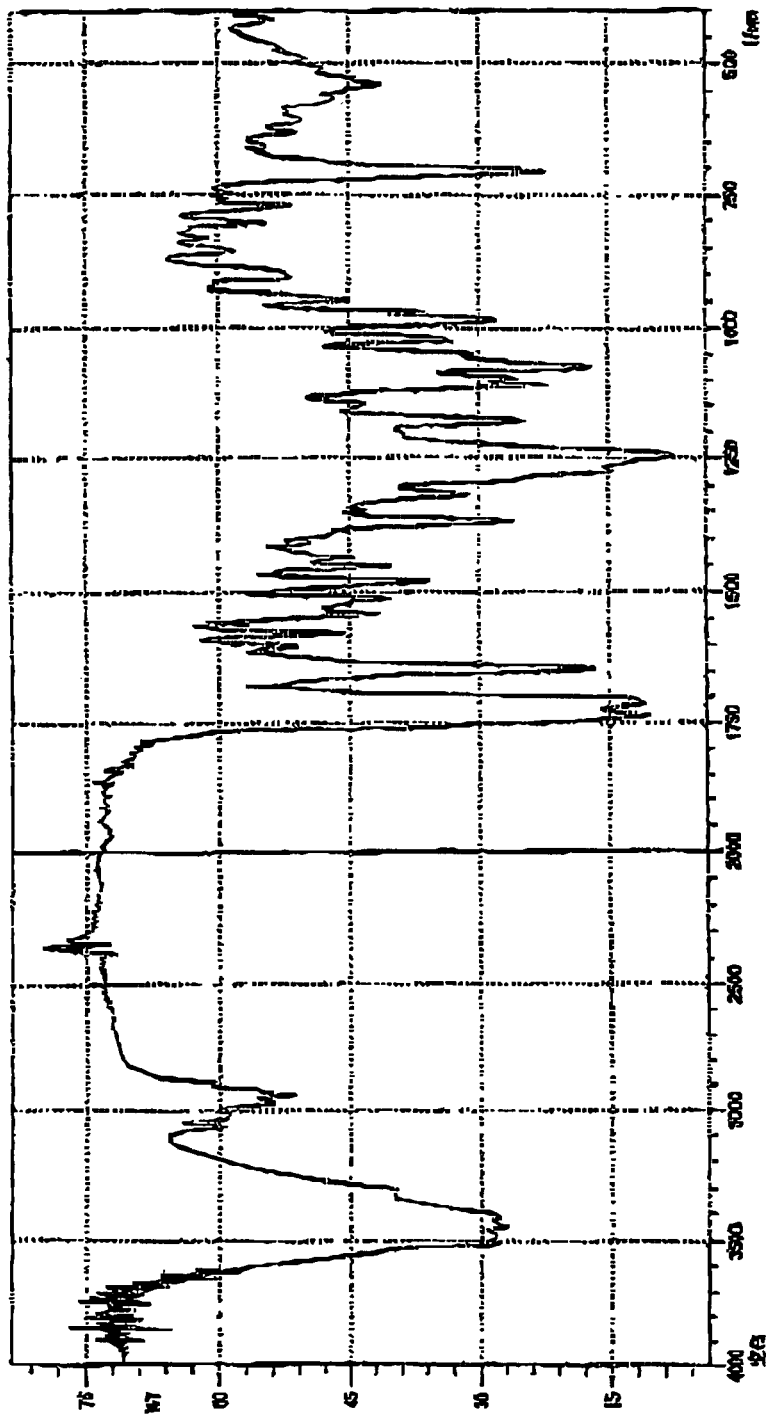
FIG. 3 shows an infrared spectrogram of the product obtained in Example 3.
Figure 4:
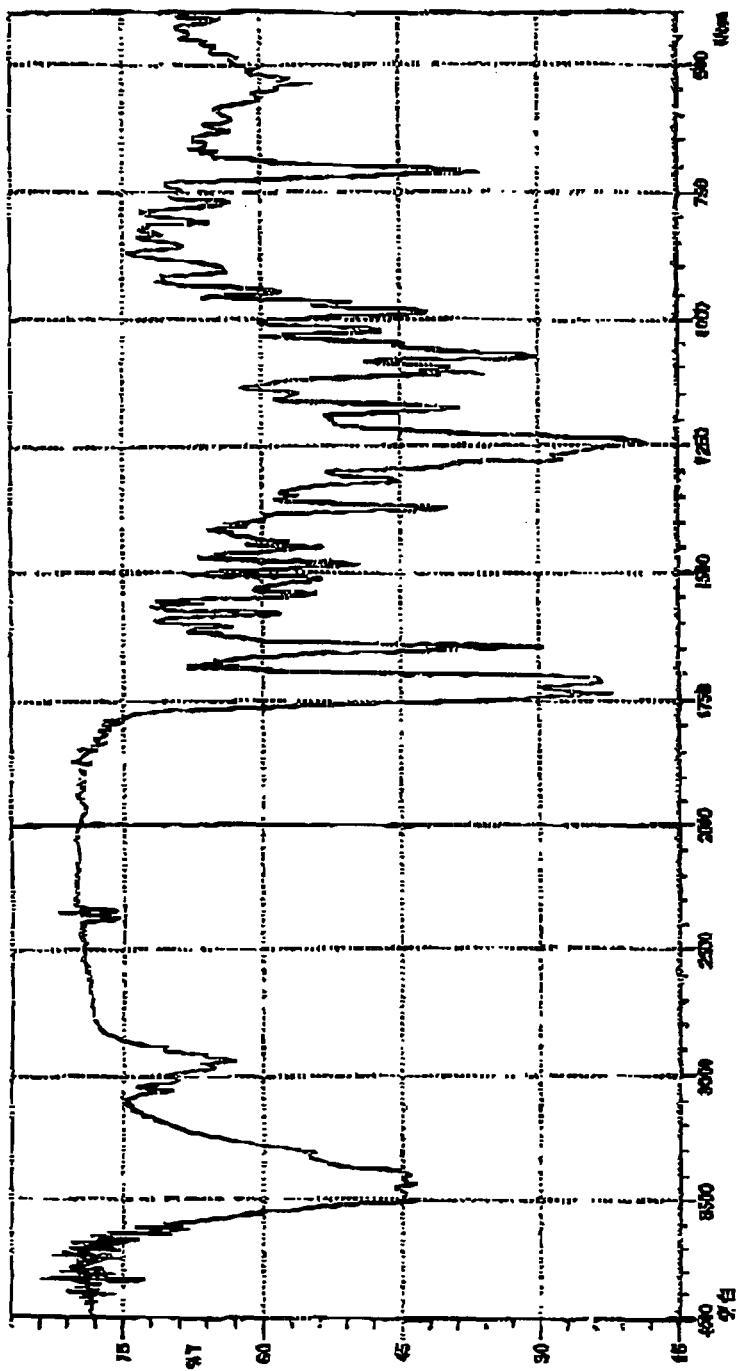
FIG. 4 shows an infrared spectrogram of the product obtained in Example 4.
Figure 5:
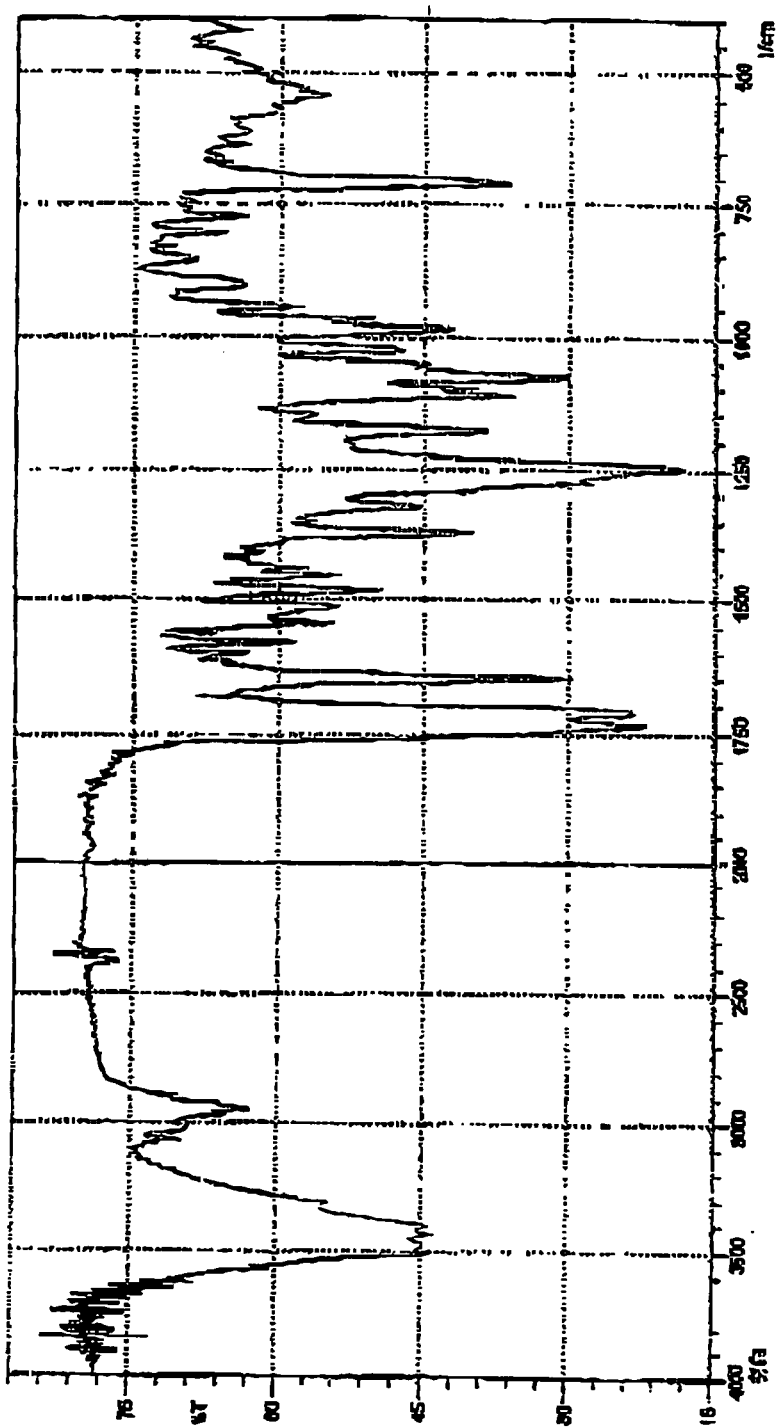
FIG. 5 shows an infrared spectrogram of the product obtained in Example 5.
Figure 6:
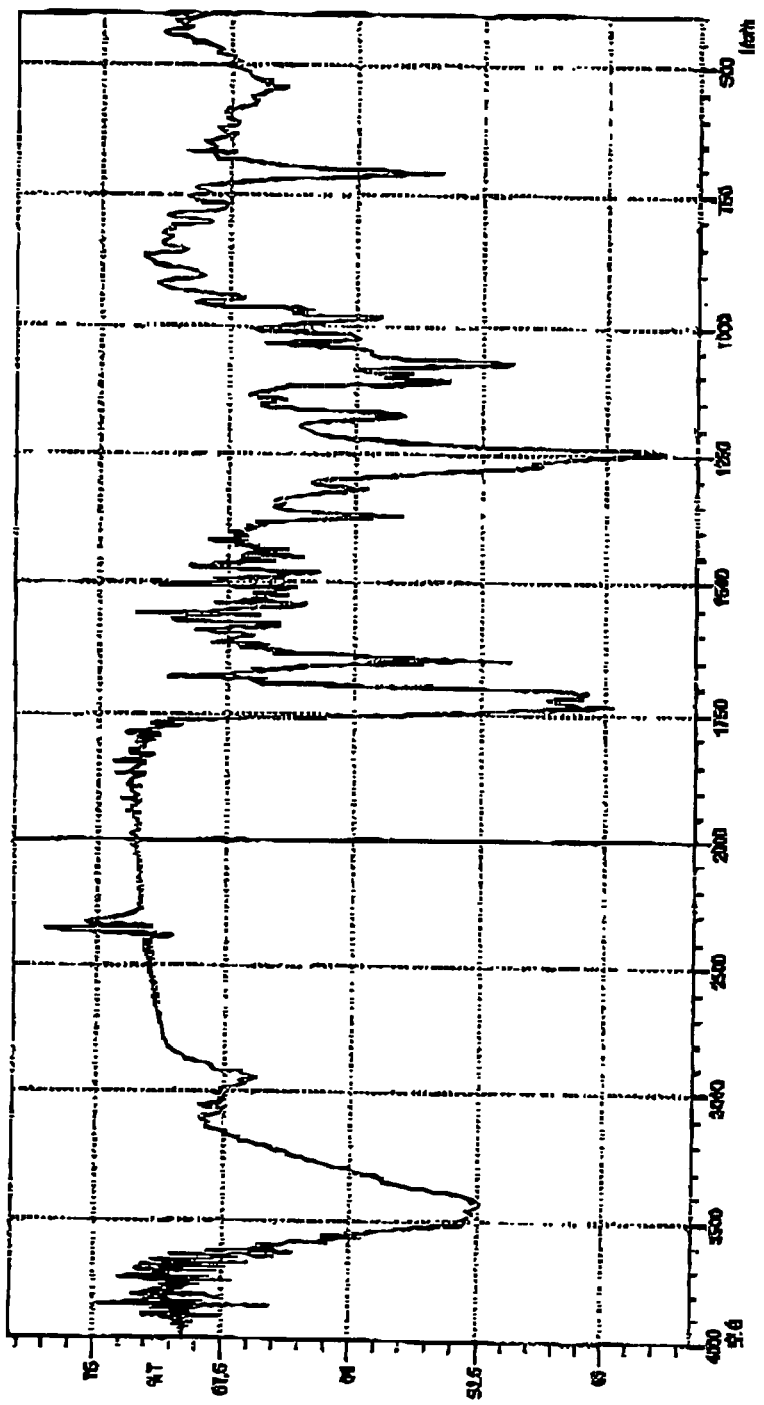
FIG. 6 shows an infrared spectrogram of the product obtained in Example 6.
Figures 1, 7:
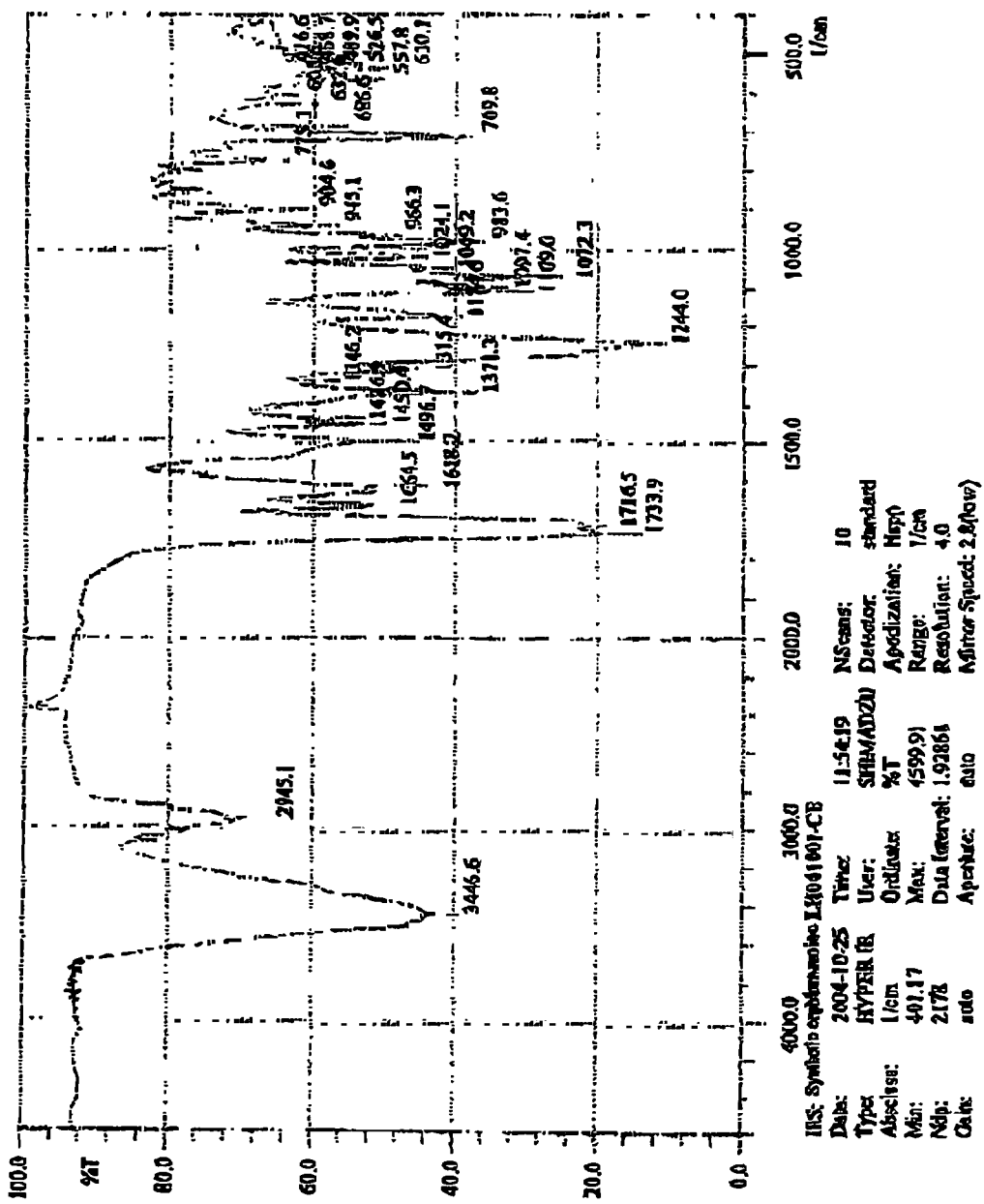
Figures 2, 7:
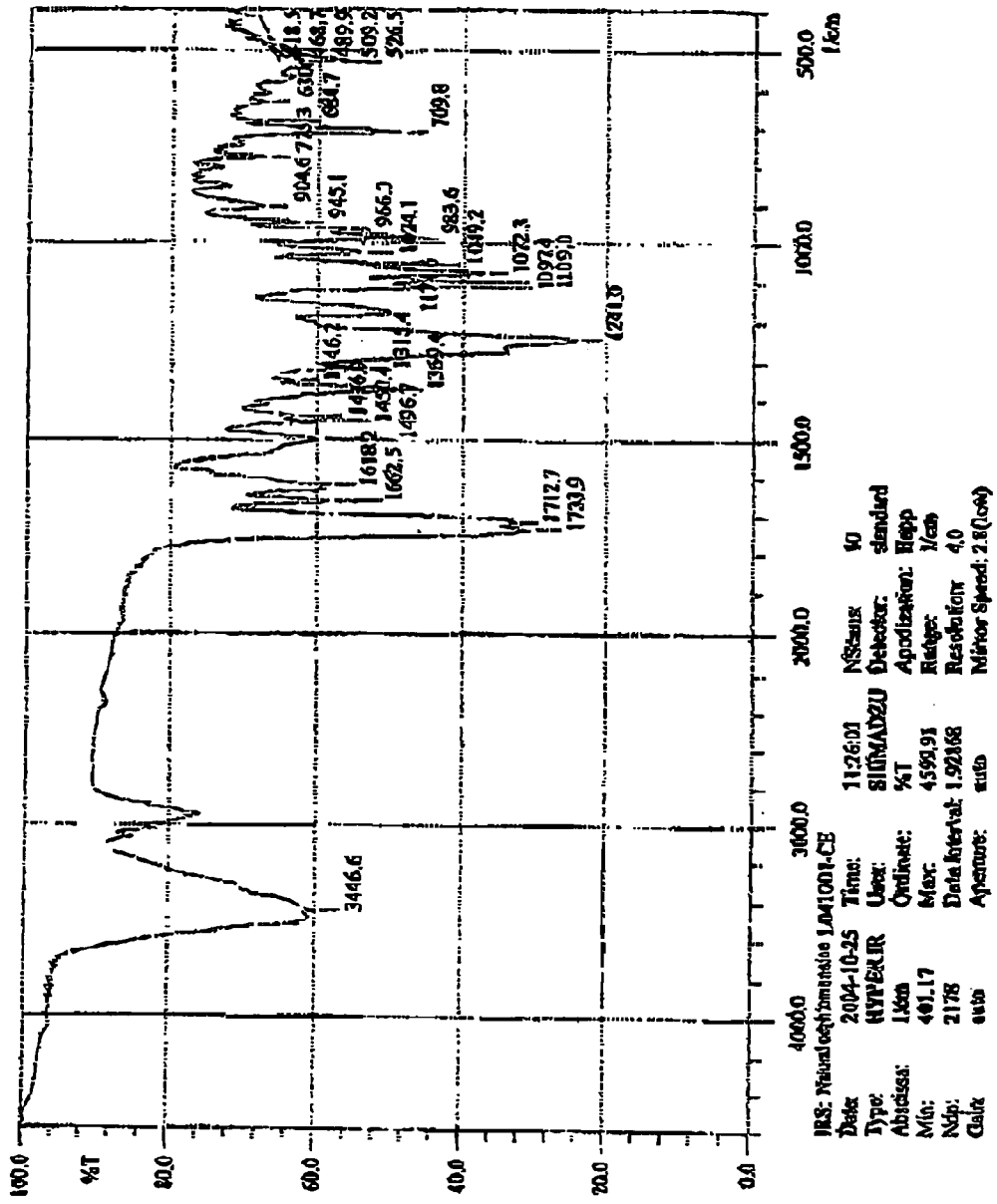
Figure 8:
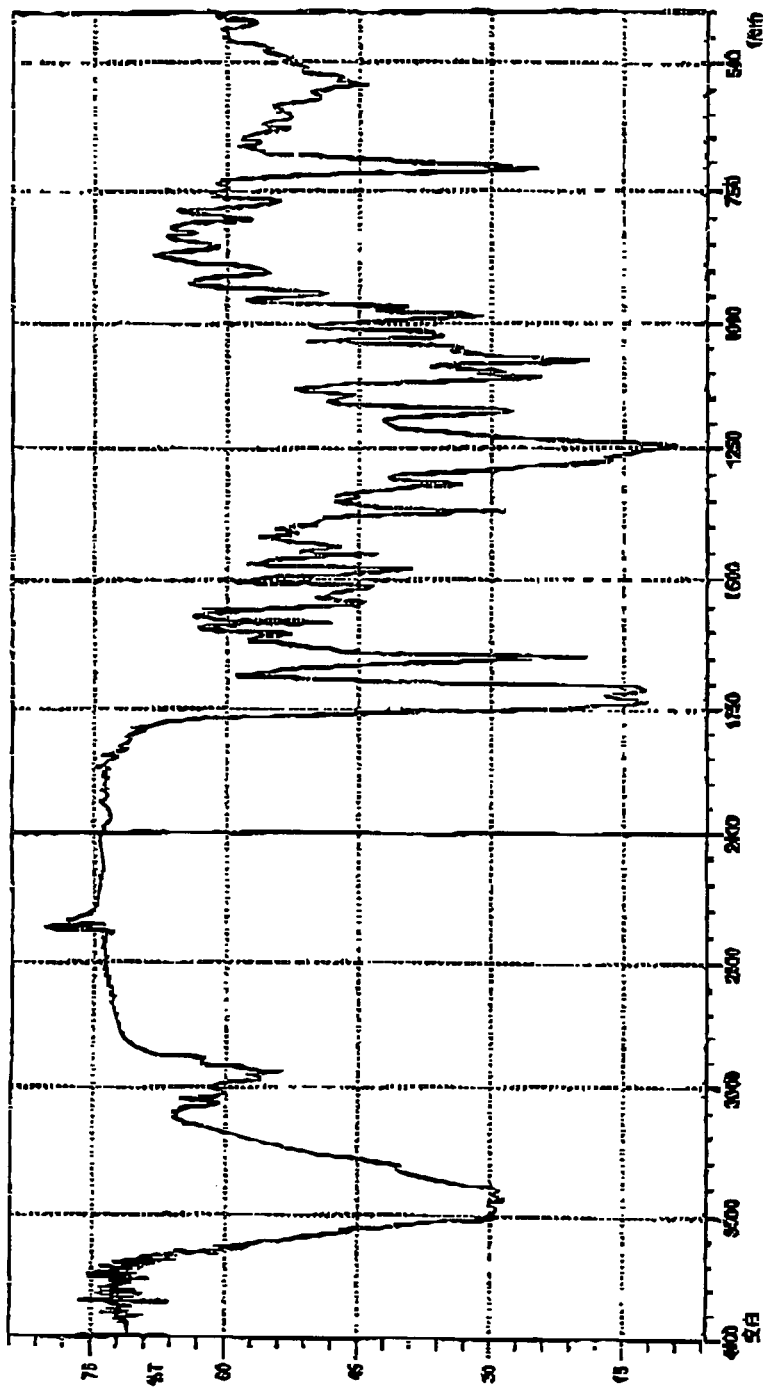
FIG. 8 shows an infrared spectrogram of the product obtained in Example 8.
Figure 9:
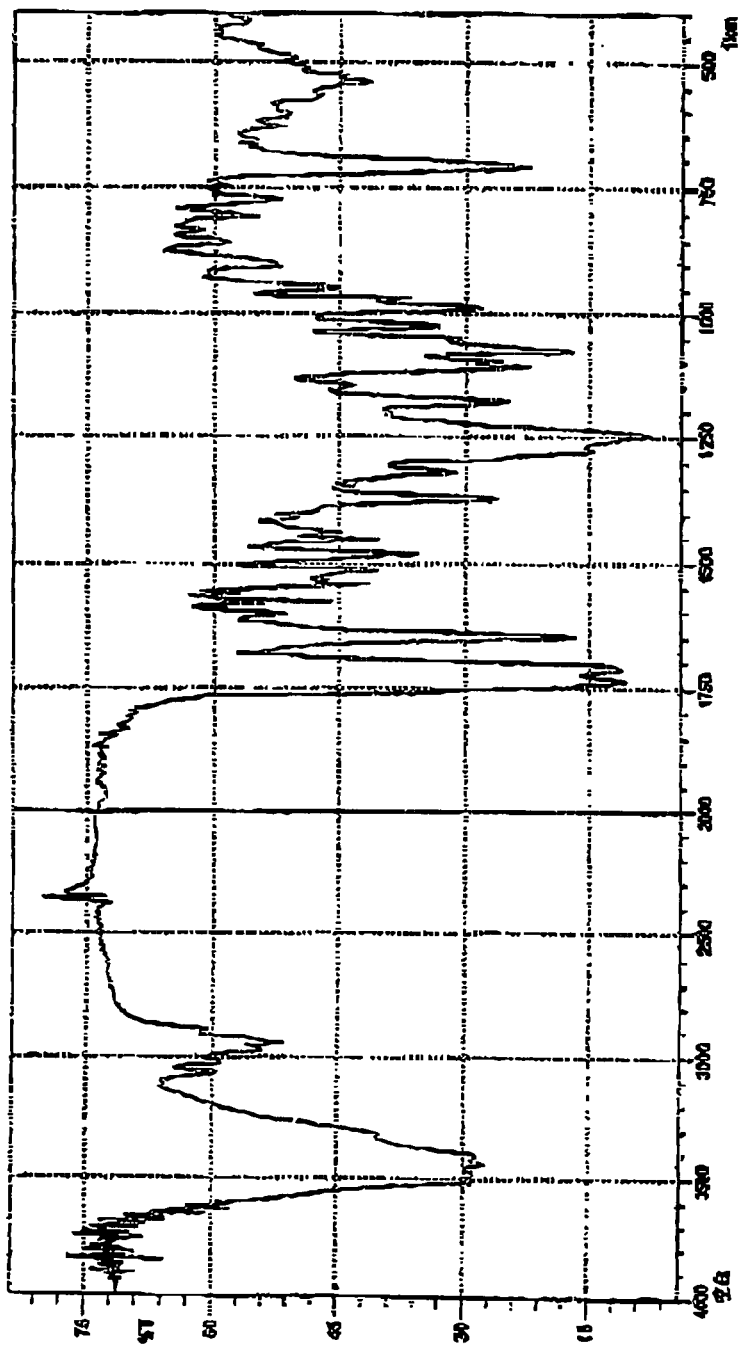
FIG. 9 shows an infrared spectrogram of the product obtained in Example 9.
Figure 10:
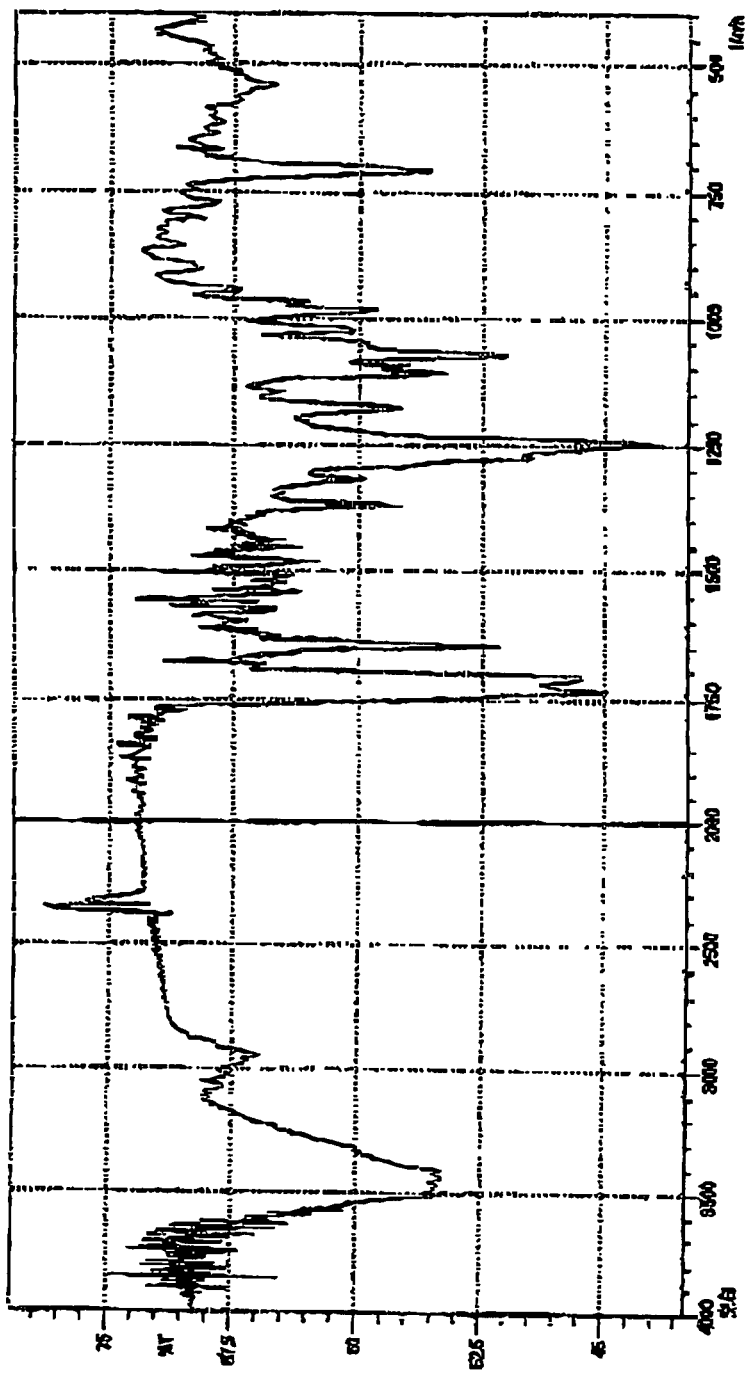
FIG. 10 shows an infrared spectrogram of natural paclitaxel.

The present invention is further illustrated by the following examples that are not intended as a limitation of the invention.

Example 1

Preparation of Paclitaxel from 10-deacetylpaclitaxel 4.5 g of 10-deacetylpaclitaxel was added to and dissolved in 100 ml of dehydrated tetrahydrofuran. While the solution was being stirred, 120 mg of cerium trichloride was added therein. Stirring was continued for 30 min at room temperature. 7.0 ml of acetic anhydride was slowly dropped into the solution after cerium trichloride was fully dispersed therein. Then stirring was continued for 2 h at room temperature. After it was detected by thin-layer chromatography (TLC) that the reaction was completely carried out, the solution was diluted with 50 ml of water. Acetic acid in the reaction mixtures was completely neutralized with saturated aqueous solution of sodium bicarbonate, and the insoluble substances produced therein were extracted with 250 ml of trichloromethane. After three extractions, the liquid extracts of trichloromethane were combined together, and concentrated to dryness under reduced pressure, yielding 4.7 g of 2',10-diacetyltaxane as a pale yellow solid.

4.7 g of 2',10-diacetyltaxane as a pale yellow solid was added to and dissolved in 200 ml of methanol. Then, the mixture was cooled in an ice bath to a temperature 3° C. or less. 200 ml of 0.4 M dimethylamine methanol having a temperature 3° C. or less was added therein, and stirring was continued for 1.5 h under the condition of ice bath at a temperature 3° C. or less. After it was detected by thin-layer chromatography (TLC) that the reaction was completely carried out, 400 ml of 0.2M aqueous HCl was added, precipitating pale yellow flocculent crystals were extracted three times with 250 ml of trichloromethane. The liquid extracts were concentrated to dryness under reduced pressure, yielding 4.6 g of 40% paclitaxel as a pale yellow solid. After purification, it could be confirmed that the product obtained above was the same in the structure as natural paclitaxel by comparing the infrared spectrum with that of natural paclitaxel.

Example 2

Preparation of Paclitaxel from 7-(1β-xyloxyl)-10-deacetylpaclitaxel

1) Pretreatment of 7-(1β-xyloxyl)-10-deacetylpaclitaxel Materials

To a solution of 60 ml of methanol/chloroform (4:1) was added 1.2 g of 7-(1β-xyloxyl)-10-deacetylpaclitaxel, and then 0.7 g of sodium periodate and 5 ml of 0.5 M sulphuric acid were added therein. The mixture was reacted at room temperature for 3 h. Then, the reaction mixture was diluted with 60 ml of water, and extracted three times with 60 ml of chloroform. The organic phase extract was concentrated to dryness, yielding 1.2 g of a colorless solid.

The solid (1.2 g) was dissolved in 40 ml of methanol. The resulting solution was mixed with 4 ml of 50% acetic acid and 0.5 ml of phenylhydrazine. The mixture was reacted at 50° C. for 2 h. Then, the reaction mixtures was diluted with 40 ml of water, and extracted three times with 40 ml of chloroform. The organic phase extract was concentrated to dryness, yielding 1.23 g of a solid. After silica gel chromatography, the chromatography liquid was concentrated to dryness, yielding 1.1 g of 10-deacetylpaclitaxel.

2) Preparation of Paclitaxel

According to the process in Example 1, 1.15 g of pale yellow paclitaxel was finally produced. After silica gel adsorption chromatography→C-18 reverse phase chromatography (acetonitrile-water)→acetone crystallization, 0.376 g of 99.6% white paclitaxel crystallisate was obtained. it could be confirmed that the product obtained above was the same in the structure as natural paclitaxel by comparing the infrared spectrum with that of natural paclitaxel, In addition, it could be demonstrated by $^1$H-NMR and $^{13}$C-NMR data that the chemical structure of white crystal sample-numbered FJ030702-5 was completely the same as that of natural paclitaxel. The experimental data and analyses were as follows.

(I) Mass Spectrum

1. High Resolution Mass Spectrum (1) Results: measured molecular weight 853.3334
theoretical molecular weigh 853.3310
measured molecular formula $C_{47}H_{51}NO_{14}$
theoretical molecular formula $C_{47}H_{51}NO_{14}$ (2) Analyses: Molecular weight measured by high resolution mass spectrum was 853.3334, so as to determine the molecular formula of $C_{47}H_{51}NO_{14}$ which was consistent with that of paclitaxels; thus it could be confirmed that sample FJ030702-5 was paclitaxel.

2. Mass Spectrum (1) Data of Measurement: ion peaks of m/z 854, 836, 776, 569, 551, 509, 286 and so on.

(2) Analyses: using cation ESI-MS method for the measurement of mass Spectrum of sample FJ030702-5; and providing molecular ion peak of m/z 854[M+H]$^+$ and main fractional peak of m/z 776[M+H—AcOH—H$_2$O]$^+$, m/z 569[M+H—ScH]$^+$, m/z 551[M+H—ScH—H$_2$O]$^+$, m/z 509[M+H—ScH—AcOH]$^+$, 286[ScH+H]$^+$, which were substantially consistent with the data in the reference document[3].

(II) Comprehensive Analyses

Molecular weight of sample FJ030702-5 measured by high resolution mass spectrum was 853.3334, so as to determine the molecular formula of $C_{47}H_{51}O_{14}N$. Four quaternary carbon methyl signals (δ 1.14, 1.24, 1.68, 1.79), 3α-H signal at δ 3.79 (d, J=6.5 Hz), and AB system doublet consisting of δ 4.19 and 4.30, which were two hydrogen atoms at C-20 position, in combination with the carbon spectrum data, showed that said compound was taxanes tricyclic diterpenoid having a four-membered oxygen ring. The signal of δ 7.01 (d, J=8.8) in the hydrogen spectrum belonged to hydrogen on nitrogen. Upon analyses in combination with mass spectrum fractions, it could be proved that the compound had nitrogen-containing side chains. It could be seen from the hydrogen spectrum that the signals of 10α-H, 13β-H, 3'-H, 2β-H, 5α-H, 2'-H and 7α-H were respectively at δ 6.27 (S), 6.23 (t, J=9.0), 5.78 (dd, J=2.5, 9.0), 5.67 (d, J=7.0), 4.94 (d, J=9.0), 4.79 (d, J=2.0) and 4.39 (dd, J=7.5, 11.0), which showed that heteroatom substitution took place at said positions. The signals of δ 79.04 and δ 81.16 in the carbon spectrum showed that there were two oxygen-containing quaternary carbons. In addition, the signals of two acetyl groups, two benzoyl groups and a mono-substituted benzene were also present in the NMR spectrum. Upon spectral analyses as stated above and by comparing with the reference values of paclitaxels (G. N. Chmumy, B. D. Hilton, S. Brobst, S. A. Look, K. M. Witherup and J. A. Brutlen. $^1$H- and $^{13}$C-NMR assignments for paclitaxel, 7-epi-paclitaxel and cephalomannine. J. Nat. Prod. 1992, 55(4), 414-423), it could be confirmed that they were substantially consistent with each other. Thus, it could be confirmed that sample FJ030702-5 had the chemical structural of paclitaxel.

TABLE 1

Comparison of the 1H-NMR Chemical Shifts of Sample FJ030702-5 with the Reference Values of Pacilitaxel (CDCl3, 500 MHz)

| Proton | Chemical shift | Coupling constant | Reference value |
|---|---|---|---|
| 2-H | 5.67 d | 7.0 | 5.67 d (7.1) |
| 3-H | 3.79 d | 6.5 | 3.79 dd (7.0. 1.0) |
| 5-H | 4.49 d | 9.0 | 4.94 dd (9.6, 2.3) |
| 6-Ha | 2.54 ddd | 7.0, 9.5, 15.0 | 2.54 ddd (6.7, 9.7, 14.8) |
| 6-Hb | 1.88 ddd | 2.0, 12.5, 14.6 | 1.88 ddd (2.3, 11.0, 14.7) |
| 7-H | 4.39 dd | 7.5, 11.0 | 4.40 dd (6.7, 10.9) |
| 10-H | 6.27 s | | 6.27 s |
| 13-H | 6.23 t | 9.0 | 6.23 tq (9.0, 1.5) |
| 14-Ha | 2.35 dd | 9.0, 15.5 | 2.35 dd (9.0, 15.4) |
| 14-Hb | 2.28 dd | 9.0, 15.5 | 2.28 ddd (0.6, 9.0, 15.3) |
| 16-CH$_3$ | 1.14 s | | 1.14 s |
| 17-CH$_3$ | 1.24 s | | 1.24 s |
| 18-CH$_3$ | 1.79 s | | 1.79 s |
| 19-CH$_3$ | 1.68 s | | 1.68 s |
| 20-Ha | 4.30 d | 8.5 | 4.30 ddd (0.8, 1.1, 8.4) |
| 20-Hb | 4.19 d | 8.5 | 4.19 dd (1.0, 8.5) |
| 2'-H | 4.79 d | 2.0 | 4.78 d (2.7) |
| 3'-H | 5.78 dd | 2.5, 9.0 | 5.78 dd (2.8, 8.9) |
| 3'-NH | 7.00 d | 9.0 | 7.01 d (8.9) |
| o-OBz | 8.13 d | 7.5 | 8.13 dd (1.3, 8.4) |
| m-OBz | 7.38-7.52 m | | 7.51 m |
| p-OBz | 7.61 t | 7.5 | 7.61 tt (1.4, 7.4) |
| o-3' Ph | 7.38-7.52 m | | 7.48 m |
| m-3' Ph | 7.38-7.52 m | | 7.42 m |
| p-3' Ph | 7.35 t | 7.5 | 7.35 tt (1.6, 7.3) |
| o-NBz | 7.74 d | 7.5 | 7.74 dd (1.2, 8.3) |
| m-NBz | 7.38-7.52 m | | 7.40 m |
| p-NBz | 7.38-7.52 m | | 7.49 m |
| 4-OAc | 2.38 s | | 2.38 s |
| 10-OAc | 2.23 s | | 2.23 s |
| 1-OH | | | 1.98 brs |
| 7-OH | | | 2.48 brs |
| 2'-OH | | | 3.61 brs |

TABLE 2

Comparison of 13C-NMR Chemical Shifts of Sample FJ030702-5 with Reference Values of Pacilitaxel (CDCl3, 125 MHz)

| Carbon atom | DEPT | Sample value | Reference value |
|---|---|---|---|
| C-1 | C | 79.04 | 79.0 |
| C-2 | CH | 74.95 | 74.9 |
| C-3 | CH | 45.63 | 45.6 |
| C-4 | C | 81.16 | 81.1 |
| C-5 | CH | 84.40 | 84.4 |
| C-6 | CH$_2$ | 35.61 | 35.6 |
| C-7 | CH | 72.17 | 72.2 |
| C-8 | C | 58.62 | 58.6 |
| C-9 | C | 203.61 | 203.6 |
| C-10 | CH | 75.56 | 75.5 |
| C-11 | C | 133.19 | 133.2 |
| C-12 | C | 141.96 | 142.0 |
| C-13 | CH | 72.36 | 72.3 |
| C-14 | CH$_2$ | 35.69 | 35.7 |
| C-15 | C | 43.17 | 43.2 |
| C-16 | CH$_3$ | 21.80 | 21.8 |
| C-17 | CH$_3$ | 26.86 | 26.6 |
| C-18 | CH$_2$ | 14.83 | 14.8 |
| C-19 | CH$_3$ | 9.55 | 9.5 |
| C-20 | CH$_2$ | 76.50 | 76.5 |
| C-1' | C | 172.70 | 172.7 |
| C-2' | CH | 73.20 | 73.2 |
| C-3' | CH | 55.04 | 55.0 |
| 4-OCOCH$_3$ | CH$_3$ | 22.62 | 22.6 |
| 10-OCOCH$_3$ | CH$_2$ | 20.84 | 20.8 |
| 4-OCOCH$_3$ | C | 170.36 | 170.4 |
| 10-OCOCH$_3$ | C | 171.24 | 171.2 |
| CO—OBz | C | 167.00 | 167.0 |
| q-OBz | C | 129.15 | 129.1 |
| o-OBz | CH | 130.20 | 130.2 |
| m-OBz | CH | 128.72 | 128.71 |
| p-OBz | CH | 133.71 | 133.7 |
| q-3' Ph | C | 133.63 | 133.6 |
| o-3' Ph | CH | 127.03 | 127.03 |
| m-3' Ph | CH | 128.69 | 128.68 |
| p-3' Ph | CH | 131.96 | 131.9 |
| CO—NBz | C | 167.05 | 167.02 |
| q-NBz | C | 137.98 | 138.0 |
| o-NBz | CH | 127.03 | 127.04 |
| m-NBz | CH | 129.02 | 129.0 |
| p-NBz | CH | 128.34 | 128.3 |

By comparing the infrared spectrum with that of natural paclitaxel, it could be confirmed that the product obtained above was the same in the structure as natural paclitaxel.

Example 3

Preparation of Paclitaxel from 10-deacetylpaclitaxel 4.5 g of 10-deacetylpaclitaxel was added to and dissolved in 100 ml of tetrahydrofuran. While the solution was being stirred, 150 mg of lanthanon chloride was added therein. Stirring was continued for 30 min at room temperature. 7.0 ml of acetic anhydride was slowly dropped into the solution after the lanthanon chloride was fully dispersed therein. Then stirring was continued for 2 h at room temperature. After it was detected by thin-layer chromatography (TLC) that the reaction was completely carried out, the solution was diluted with 50 ml of water. Acetic acid in the reaction mixtures was completely neutralized with saturated aqueous solution of sodium bicarbonate, and insoluble substances produced therein were extracted with 250 ml of trichloromethane. After three extractions, the liquid extracts of trichloromethane were combined together, and concentrated to dryness under reduced pressure, yielding 4.74 g of 2',10-diacetyltaxane as a pale yellow solid.

To 200 ml of methanol was added 4.74 g of 2',10-diacetyl-taxane as a pale yellow solid, and solved therein. Then, the mixture was cooled in an ice bath to a temperature 3° C. or less. 200 ml of 0.4 M dimethylamine methanol having a temperature 3° C. or less was added therein, and stirring was continued for 1.5 h under the condition of ice bath at a temperature 3° C. or less. After it was detected by thin-layer chromatography (TLC) that the reaction was completely carried out, 400 ml of 0.2M aqueous HCl was added. Then the obtained flocculent crystals were extracted with 250 ml of trichloromethane for three times. The liquid extracts were concentrated to dryness under reduced pressure, yielding 4.65 g of 39.1% paclitaxel as a pale yellow solid. After purification, it could be confirmed that the product obtained above was the same in the structure as natural paclitaxel by comparing the infrared spectrum with that of natural paclitaxel.

Example 4

Preparation of Paclitaxel from 10-deacetylpaclitaxel 4.5 g of 10-deacetylpaclitaxel was added to and dissolved in 100 ml of tetrahydrofuran. While the solution was being stirred, 140 mg of lanthanon hydroxide was added therein. Stirring was continued for 30 min at room temperature. 7.0 ml of acetic anhydride was slowly dropped into the solution after lanthanon hydroxide was fully dispersed therein. Then stirring was continued for 2 h at room temperature. After it was detected by thin-layer chromatography (TLC) that the reaction was completely carried out, the solution was diluted with 50 ml of water. Acetic acid in the reaction mixtures was completely neutralized with saturated aqueous solution of sodium bicarbonate, and the insoluble substances produced therein were extracted with 250 ml of trichloromethane. After three extractions, the liquid extracts of trichloromethane were combined together, and concentrated to dryness under reduced pressure, yielding 4.75 g of 2',10-diacetyl-taxane as a pale yellow solid.

4.75 g of 2',10-diacetyltaxane as a pale yellow solid was added to and dissolved in 200 ml of methanol. Then, the mixture was cooled in an ice bath to a temperature 3° C. or less. 200 ml of 0.4 M dimethylamine methanol at a temperature 3° C. or less was added therein, and stirring was continued for 1.5 h under the condition of ice bath at a temperature 3° C. or less. After it was detected by thin-layer chromatography (TLC) that the reaction was completely carried out, 400 ml of 0.2M aqueous HCl was added. Then the obtained flocculent crystals were extracted three times with 250 ml of trichloromethane. The liquid extracts were concentrated to dryness under reduced pressure, yielding 4.68 g of 39.6% paclitaxel as a pale yellow solid. After purification, it could be confirmed mat the product obtained above was the same in the structure as natural paclitaxel by comparing the infrared spectrum with that of natural paclitaxel.

Example 5

Preparation of Paclitaxel from 10-deacetylpaclitaxel 4.5 g of 10-deacetylpaclitaxel was added to and dissolved in 100 ml of tetrahydrofuran. While the solution was being stirred, 200 mg of lanthanon sodium sulfate double salt was added therein. Stirring was continued for 30 min at room temperature. 7.0 ml of acetic anhydride was slowly dropped into the solution after the lanthanon sodium sulfate double salt was fully dispersed therein. Then stirring was continued for 2 h at room temperature. After it was detected by thin-layer chromatography (TLC) that the reaction was completely carried out, the solution was diluted with 50 ml of water. Acetic acid in the reaction mixtures was completely neutralized with saturated aqueous solution of sodium bicarbonate, and the insoluble substances produced therein were extracted with 250 ml of trichloromethane. After three extractions, the liquid extracts of trichloromethane were combined together, and concentrated to dryness under reduced pressure, yielding 4.67 g of 2',10-diacetyltaxane as a pale yellow solid.

4.67 g of 2',10-diacetyltaxane as a pale yellow solid was added to and dissolved in 200 ml of methanol. Then, the mixture was cooled in an ice bath to a temperature 3° C. or less. 200 ml of 0.4 M dimethylamine methanol having a temperature 3° C. or less was added therein, and stirring was continued for 1.5 h under the condition of ice bath at a temperature 3° C. or less. After it was detected by thin-layer chromatography (TLC) that the reaction was completely carried out, 400 ml of 0.2M aqueous HCl was added. Then the obtained flocculent crystals were extracted three times with 250 ml of trichloromethane. The liquid extracts were concentrated to dryness under reduced pressure, yielding 4.56 g of 39.6% paclitaxel as a pale yellow solid. After purification, it could be confirmed that the product obtained above was the same in the structure as natural paclitaxel by comparing the infrared spectrum with that of natural paclitaxel.

Example 6

Preparation of Paclitaxel from 10-deacetylpaclitaxel 4.5 g of 10-deacetylpaclitaxel was added to and dissolved in 100 ml of tetrahydrofuran, and solved therein. While the solution was being stirred, 200 mg of lanthanon ammonium sulfate double salt was added therein. Stirring was continued for 30 min at room temperature. 7.0 ml of acetic anhydride was slowly dropped into the solution after lanthanon ammonium sulfate double salt was fully dispersed therein. Then stirring was continued for 2 h at room temperature. After it was detected by thin-layer chromatography (TLC) that the reaction was completely carried out, the solution was diluted with 50 ml of water. Acetic acid in the reaction mixtures was completely neutralized with saturated aqueous solution of sodium bicarbonate, and the insoluble substances produced therein were extracted with 250 ml of trichloromethane. After three extractions, liquid extracts of trichloromethane were combined together, and concentrated to dryness under reduced pressure, yielding 4.7 g of 2',10-diacetyltaxane as a pale yellow solid.

4.7 g of 2',10-diacetyltaxane as a pale yellow solid was added to and dissolved in 200 ml of methanol. Then, the mixture was cooled in an ice bath to a temperature 3° C. or less. 200 ml of 0.4 M dimethylamine methanol having a temperature 3° C. or less was added therein, and stirring was continued for 1.5 h under the condition of ice bath at a temperature 3° C. or less. After it was detected by thin-layer chromatography (TLC) that the reaction was completely carried out, 400 ml of 0.2M aqueous HCl was added. Then the obtained flocculent crystals were extracted three times with 250 ml of trichloromethane. The liquid extracts were concentrated to dryness under reduced pressure, yielding 4.6 g of 38.6% paclitaxel as a pale yellow solid. After purification, it could be confirmed that the product obtained above was the same in the structure as natural paclitaxel by comparing the infrared spectrum with that of natural paclitaxel.

Example 7

Preparation of Cephalomannine from 10-deacetylcephalomannine 4.5 g of 10-deacetylcephalomannine was added to and dissolved in 100 ml of tetrahydrofuran, and solved therein. While the solution was being stirred, 120 mg of cerium trichloride was added therein. Stirring was continued for 30 min at room temperature. 7.0 ml of acetic anhydride was slowly dropped into the solution after cerium trichloride was fully dispersed therein. Then stirring was continued for 2 h at room temperature. After it was detected by thin-layer chromatography (TLC) that the reaction was completely carried out, the solution was diluted with 50 ml of water. Acetic acid in the reaction mixtures was completely neutralized with a saturated aqueous solution of sodium bicarbonate, and insoluble substances produced therein were extracted with 250 ml of trichloromethane. After three extractions, the liquid extracts of trichloromethane were combined together, and concentrated to dryness under reduced pressure, yielding 4.71 g of pale yellow 2',10-diacetylcephalomannine analog solid.

4.71 g of 2',10-diacetylcephalomannine analog solid was added to and dissolved in 200 ml of methanol. Then, the mixture was cooled in an ice bath to a temperature 3° C. or less. 200 ml of 0.4 M dimethylamine methanol at a temperature 3° C. or less was added therein, and stirring was continued for 1.5 h under the condition of ice bath at a temperature 3° C. or less. After it was detected by thin-layer chromatography (TLC) that the reaction was completely carried out, 400 ml of 0.2M aqueous HCl was added. Then the obtained flocculent crystals were extracted three times with 250 ml of trichloromethane. The liquid extracts were concentrated to dryness under reduced pressure, yielding 4.63 g of pale yellow cephalomannine solid. After silica gel adsorption chromatography→C-18 reverse phase chromatography (acetonitrile-water)→acetone crystallization, 3.24 g of 97.7% white cephalomannine crystallisate was obtained. By comparing the infrared spectrum with that of natural cephalomannine, it could be confirmed that the product obtained above was the same in the structure as natural cephalomannine.

Example 8

Preparation of Paclitaxel from 10-deacetylpaclitaxel 5.0 g of 45% 10-deactylpaclitaxel was added to and dissolved in 20 ml of pyridine, and solved therein. While the solution was being stirred, 150 mg of cerium trichloride was added therein. Stirring was continued for 30 min at room temperature. 8.0 ml of acetic anhydride was slowly dropped into the solution after a cerium trichloride was fully dispersed therein. Then stirring was continued for 2 h at room temperature. After it was detected by thin-layer chromatography (TLC) that the reaction was completely carried out, the solution was diluted with water. The precipitates were filtered under reduced pressure to dryness, yielding 5.1 g of 2',10-diacetyltaxane as a pale yellow solid.

5.1 g of 2',10-diacetyltaxane as a pale yellow solid was added to and dissolved in 200 ml of methanol. Then, the mixture was cooled in an ice bath to a temperature 3° C. or less. 200 ml of 0.4 M dimethylamine methanol having a temperature 3° C. or less was added therein, and stirring was continued for 1.5 h under the condition of ice bath at a temperature 3° C. or less. After it was detected by thin-layer chromatography (TLC) that the reaction was completely carried out, 400 ml of 0.2M aqueous HCl was added. Then the obtained flocculent crystals were extracted three times with 250 ml of trichloromethane. The liquid extracts were concentrated to dryness under reduced pressure, yielding 4.5 g of 41.6% paclitaxel as a pale yellow solid. After purification, it could be confirmed that the product obtained above was the same in the structure as natural paclitaxel by comparing the infrared spectrum with that of natural paclitaxel.

Example 9

Preparation of Paclitaxel from 10-deacetylpaclitaxel 5.0 g of 82.6% 10-deacetylpaclitaxel was added to and dissolved in 100 ml of tetrahydrofuran. After 5.0 g of chloroacetamide was added therein, the mixture was heated to 100° C., stirred and reacted for 3 h. Then, the mixture was diluted with water. The solid substance obtained after filtration under reduced pressure was chromatographied with 100 g of silica gel column, and eluted with dichloromethane/ethyl acetate (7:3). The active fraction was concentrated under reduced pressure to dryness, yielding a solid substance. By the re-crystallization of said solid substance with acetone/petroleum ether, 5.0 g of the product was obtained. Subsequently, the product was dissolved in 100 ml of tetrahydrofuran, and 20 ml of acetic anhydride was added therein. The mixture was heated to 100° C. and reacted for 3 h.

The product obtained above was dissolved in 100 ml of methanol. After 2.0 g of thiourea and 1.0 g of sodium bicarbonate were added therein, the mixture was stirred at room temperature. After the reaction was carried out for 1 h, the mixture was diluted with water, yielding a precipitate. By acetone/light oil re-crystallization of the solid obtained by filtering the precipitate, 3.3 g of 98.6% paclitaxel solid was obtained. By comparing the infrared spectrum with that of natural paclitaxel, it could be confirmed that the product obtained above was the same in the structure as natural paclitaxel.

Comparative Example 1

According to the Process as Disclosed in U.S. Pat. No. 5,200,534A

Preparation of Paclitaxel from 10-deacetylpaclitaxel 0.5 g of 10-deacetylpaclitaxel was dissolved in 2 ml of pyridine. After 0.5 g of chloroacetamide was added therein, the mixture was reacted at room temperature for 1 h. Then, the mixture was diluted with water. The solid substance obtained after filtration under reduced pressure was chromatographied with 10 g of silica gel column, and eluted with trichloromethane/acetone (2-5%). The active fraction was concentrated under reduced pressure to dryness, yielding a solid substance. After the re-crystallization of said solid substance with acetone/normal hexane, 0.5 g of the product was obtained. Subsequently, the product was dissolved in 1 ml of pyridine. After 2 ml of acetic anhydride was added therein, the mixture was heated to 100° C. and reacted for 30 min.

0.2 g of said product obtained above was dissolved in 10 ml of methanol. Then 0.2 g of thiourea and 0.1 of sodium bicarbonate were added therein, and the mixture was stirred at room temperature. After the reaction was carried out for 1 h, the mixture was diluted with water, yielding a precipitate. By acetone/light oil re-crystallization of the solid obtained by filtering the precipitate, 0.3 g of paclitaxel was obtained.

Comparative Example 2

According to the Process as Disclosed in U.S. Pat. No. 5,200,534A

Preparation of Paclitaxel from 7-(1β-xyloxyl)-10-deacetylpaclitaxel 1 g of 7-(1β-xyloxyl)-10-deacetylpaclitaxel was dissolved in 50 ml of a methanol/chloroform solution (4:1). Then, 0.6 g of sodium periodate and 4 ml of 1N sulphuric acid were added therein. The oscillating reactions of the mixtures continued for 3 h at room temperature. Subsequently, the reaction mixture was diluted with 50 ml of water, and extracted twice with 50 ml of chloroform. The organic phase extract was concentrated to dryness, yielding 1.0 g of a white solid.

Said solid was dissolved in 1 ml of pyridine, and 5 ml of acetic anhydride was then added therein. The mixture was heated to 100° C. and reacted for 30 min. After being cooled, the mixture was diluted with 50 ml of water, and filtered to yield 1.0 g of a solid. Then, said solid was dissolved in 20 ml of methanol, and 3.0 ml of acetic acid and 0.5 ml of phenylhydrazine were added therein. The resulting mixture was heated to 50-60° C., and reacted for about 3 h, and cooled. The Comparative Example 3

According to the Process as Disclosed in U.S. Pat. No. 5,200,534A

Preparation of Paclitaxel from 2'-acetylpaclitaxel 0.2 g of 2'-acetylpaclitaxel solid was dissolved in 10 ml of methanol. After 0.2% dimethylamine solution was added therein, the reaction was carried out. After it was detected by thin-layer chromatography (TLC) that the hydrolysis reaction was completely carried out, the reaction mixture was concentrated under reduced pressure to dryness, yielding a solid substance. By recrystallizing said solid substance with acetone/light oil, 0.12 g of white paclitaxel solid was obtained.

Comparative results of the present invention to the prior art.

|  | Starting materials | Products | Yields | Protecting agents | Deprotecting agents | Acylation media |
| --- | --- | --- | --- | --- | --- | --- |
| Example 1 | 10-deacetylpaclitaxel 4.5 g × 45% | paclitaxel 4.6 g × 40% | 90.9% | cerium trichloride | none | Dehydrated tetrahydrofuran |
| Example 2 | 7-(1β-xyloxyl)-10-deacetylpaclitaxel 1.2 g | paclitaxel 0.376 g × 99.6% | 31.2% | cerium trichloride | none | Dehydrated tetrahydrofuran |
| Example 3 | 10-deacetylpaclitaxel 4.5 g × 45% | Paclitaxel 4.65 g × 39.1% | 89.8% | lanthanon chloride | none | tetrahydrofuran |
| Example 4 | 10-deacetylpaclitaxel 4.5 g × 45% | Paclitaxel 4.68 g × 39.6% | 91.5% | lanthanon hydroxide | none | tetrahydrofuran |
| Example 5 | 10-deacetylpaclitaxel 4.5 g × 45% | paclitaxel 4.56 g × 39.6% | 89.2% | lanthanon sodium sulfate double salt | none | tetrahydrofuran |
| Example 6 | 10-deacetylpaclitaxel 4.5 g × 45% | paclitaxel 4.6 g × 38.6% | 87.7% | lanthanon ammonium sulfate double salt | none | tetrahydrofuran |
| Example 7 | 10-deacetylcephalomannine 4.5 g × 86.4% | Cephalomannine 3.24 g × 97.7% | 81.4% | cerium trichloride | none | tetrahydrofuran |
| Example 8 | 10-deacetylpaclitaxel 5.0 g × 45% | Paclitaxel 4.5 g × 41.6% | 83.2% | cerium trichloride | none | pyridine |
| Example 9 | 10-deacetylpaclitaxel 5.0 g × 82.6% | Paclitaxel 3.3 g × 98.6% | 78.8% | Chloroacetamide | thiourea | tetrahydrofuran |
| Comparative Example 1 | 10-deacetylpaclitaxel 0.5 g | Paclitaxel 0.3 g | 60.0% | Chloroacetamide | thiourea | pyridine |
| Comparative Example 2 | 7-(1β-xyloxyl)-10-deacetylpaclitaxel 1 g | 2'-acetyl-paclitaxel 0.4 g paclitaxel 0.1 g | 34.0% after comprehensive calculation | — | — | pyridine |
| Comparative Example 3 | 2'-acetylpaclitaxel 0.2 g | paclitaxel 0.12 g | | — | — | pyridine | reaction mixture was diluted with 20 ml of water, and extracted twice with 20 ml of trichloromethane. The organic phase liquid extract was concentrated under reduced pressure to dryness, yield a solid substance. Said solid substance was chromatographied with C-8 reverse phase column, and gradually eluted with 25%, 30%, 35%, 40%, 45% and 50% acetonitrile/water. The active fraction was concentrated under reduced pressure. 0.1 g of paclitaxel was obtained from the fraction eluted firstly; 0.5 g of a solid containing 2'-acetylpaclitaxel was obtained from the fraction eluted later, and then said solid was re-crystallized with acetonitrile/light oil to yield 0.4 g of a white solid substance.

What is claimed is:

1. A process for the preparation of synthetic taxanes, comprising: (1) selectively protecting the C(7) position on a taxane raw material bearing side chains comprising C(7)-OH, C(10)-OH and C(13) having C(2')-OH using a protecting agent; (2) acylating the C(10) and C(2')-OHs using an acylating agent; and (3) deprotecting the protecting agent at the C(7)-position to reduce to C(7)-OH, characterized in that said protecting agent is a lanthanon compound.

2. The process for the preparation of synthetic taxanes according to claim 1, characterized in that said lanthanon compound as the protecting agent is selected from the group consisting of a salt of lanthanon, a double salt of lanthanon, an alkaline compound of lanthanon, a lanthanon chloride and a lanthanon oxychloride.

3. The process for the preparation of synthetic taxanes accounding to claim 1, characterized in that said lanthanon compound as the protecting agent is selected from the group consisting of a lanthanon chloride, a lanthanon hydroxide, a lanthanon oxychloride and a lanthanon sulfate double salt.

4. The process for the preparation of synthetic taxanes according to claim 1, characterized in that said lanthanon compound as the protecting agent is a lanthanon chloride.

5. The process for the preparation of synthetic taxanes according to claim 1, characterized in that said lanthanon compound as the protecting agent is a cerium salt.

6. The process for the preparation of synthetic taxanes according to claim 1, characterized in that said lanthanon compound as the protecting agent is cerium trichloride.

7. The process for the preparation of synthetic taxanes according to claim 1, characterized in using 10-deacetylpaclitaxel or 10-deacetylcephalomannine as the raw material.

8. The process for the preparation of synthetic taxanes according to claim 1, characterized in that said synthetic taxanes are paclitaxels.

9. The process for the preparation of synthetic taxanes according to claim 7, characterized in that said synthetic taxanes are paclitaxels.

10. The process for the preparation of synthetic taxanes according to claim 1, characterized in using tetrahydrofuran as a medium for acylation.

11. The process for the preparation of synthetic taxanes according to claim 7, characterized in using tetrahydrofuran as a medium for acylation.

12. The process for the preparation of synthetic taxanes according to claim 8, characterized in using tetrahydrofuran as a medium for acylation.

13. The process for the preparation of synthetic taxanes according to claim 9, characterized in using tetrahydrofuran as a medium for acylation.

14. The process for the preparation of synthetic taxanes according to claim 10, characterized in pre-dehydrating said tetrahydrofuran.

15. The process for the preparation of synthetic taxanes according to claim 11, characterized in pre-dehydrating said tetrahydrofuran.

16. The process for the preparation of synthetic taxanes according to claim 12, characterized in pre-dehydrating said tetrahydrofuran.

17. The process for the preparation of synthetic taxanes according to claim 13, characterized in pre-dehydrating said tetrahydrofuran.

18. A process for the preparation of synthetic taxanes, comprising: (1) selectively protecting the C(7) position on a taxane raw material bearing side chains comprising C(7)-OH, C(10)-OH and C(13) having C(2')-OH using a protecting agent; (2) acylating the C(10) and C(2')-OHs using an acylating agent; and (3) deprotecting the protecting agent at the C(7)-position to reduce to C(7)-OH, characterized in that said protecting agent is a lanthanon compound, the process comprising the steps of:
  a) dissolving the raw material in tetrahydrofuran;
  b) adding lanthanon compounds for the protection of the C(7)-OH;
  c) acylating by adding the acylating agent;
  d) neutralizing with an alkali after the acylation;
  e) extracting to an extract phase with an organic solvent insoluble with tetrahydrofuran;
  f) removing the organic solvent in the extract phase to obtain 2',10-diacyltaxane product;
  g) dissolving the product in step f) in an inert solvent;
  h) selectively hydrolyzing an ester group at position C(2') with a weak aqueous alkali dissolved in the inert solvent in step (g), and meanwhile deprotecting the protecting agent of C(7)-OH;
  i) neutralizing with an acid;
  j) extracting to a second extract phase with an organic solvent insoluble with the inert solvent in step g) and water; and
  k) removing the organic solvent in the second extract phase to obtain C(10) acylated taxanes bearing C(7)-OH and a C(13) side chain having C(2')-OH.

19. The process according to claim 18, wherein the tetrahydrofuran in step (a) is pre-dehydrated; the organic solvent insoluble with tetrahydrofuran in step (e) is selected from the group consisting of dichloromethane and trichloromethane; the inert solvent dissolving 2',10-diacyltaxane in step g) is alcohol; the weak alkali selectively hydrolyzing acyl esters at position C(2'3) in step h) is selected from the group consisting of sodium bicarbonate, potassium bicarbonate, dimethylamine, diethylamine and aniline; and the organic solvent insoluble with the inert solvent and water in step j) is trichloromethane.

20. The process according to claim 19, wherein taxanes as the raw material bearing C(7)-OH, C(10)-OH and C(13) side chain having C(2')-OH are natural or processed 10-deacetylpaclitaxel or 10-deacetylcephalomannine.

21. The process according to claim 20, characterized in that the acylation is conducted at a room temperature, and the selective hydrolysis is conducted at a temperature $\leqq 3°$ C.

22. The process according to claim 18, wherein the synthetic taxanes are paclitaxels.

23. The process according to claim 19, wherein the synthetic taxanes are paclitaxels.

24. The process according to claim 20, wherein the synthetic taxanes are paclitaxels.

25. The process according to claim 21, wherein the synthetic taxanes are paclitaxels.

* * * * *